US00PP27380P2

(12) United States Plant Patent
Misato

(10) Patent No.: US PP27,380 P2
(45) Date of Patent: Nov. 15, 2016

(54) ***MANDEVILLA* PLANT NAMED 'SUNPARAJAPI'**

(50) Latin Name: *Mandevilla hybrida*
Varietal Denomination: Sunparajapi

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 116 days.

(21) Appl. No.: 14/544,307

(22) Filed: Dec. 20, 2014

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Anne Grunberg
(74) *Attorney, Agent, or Firm* — C. A. Whealy

(57) ABSTRACT

A new and distinct cultivar of *Mandevilla* plant named 'Sunparajapi', characterized by its vining plant habit; vigorous growth habit; freely branching habit; large dark green-colored leaves; freely flowering habit; long flowering period; and large pink-colored flowers.

1 Drawing Sheet

Botanical designation: *Mandevilla hybrida.*
Cultivar denomination: 'SUNPARAJAPI'.

BACKGROUND OF THE INVENTION

The present invention relates to a new and distinct cultivar of *Mandevilla* plant, botanically known as *Mandevilla hybrida* and hereinafter referred to by the name 'Sunparajapi'.

The new *Mandevilla* plant is a product of a planned breeding program conducted by the Inventor in Higashiomi, Shiga, Japan. The objective of the breeding program is to create new freely-branching and vining *Mandevilla* plants with large leaves and numerous large attractive flowers.

The new *Mandevilla* plant originated from a cross-pollination in Higashiomi, Shiga, Japan in April, 2006 of a proprietary selection of *Mandevilla hybrida* identified as code number MH-7, not patented, as the female, or seed parent with a proprietary selection of *Mandevilla hybrida* identified as code number MH-31, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2009.

Asexual reproduction of the new *Mandevilla* plant by cuttings in Higashiomi, Shiga, Japan since October, 2009 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparajapi'. These characteristics in combination distinguish 'Sunparajapi' as a new and distinct *Mandevilla* plant:

1. Vining plant habit.
2. Vigorous growth habit.
3. Freely branching habit.
4. Large dark green-colored leaves.
5. Freely flowering habit.
6. Long flowering period.
7. Large pink-colored flowers.

Plants of the new *Mandevilla* can be compared to plants of the female parent selection. Plants of the new *Mandevilla* differ primarily from plants of the female parent selection in the following characteristics:

1. Leaves of plants of the new *Mandevilla* are not as glossy as leaves of plants of the female parent selection.
2. Plants of the new *Mandevilla* and the female parent selection differ in flower color as plants of the female parent selection have white-colored flowers.

Plants of the new *Mandevilla* can be compared to plants of the male parent selection. Plants of the new *Mandevilla* differ primarily from plants of the male parent selection in the following characteristics:

1. Leaves of plants of the new *Mandevilla* are glossier than leaves of plants of the male parent selection.
2. Plants of the new *Mandevilla* and the male parent selection differ in flower color as plants of the male parent selection have darker pink-colored flowers.

Plants of the new *Mandevilla* can be compared to plants of the *Mandevilla hybrida* 'Sunparaoros', disclosed in U.S. Plant Pat. No. 25,207. In side-by-side comparisons conducted in Higashiomi, Shiga, Japan, plants of the new *Mandevilla* differed from plants of 'Sunparaoros' in the following characteristics:

1. Plants of the new *Mandevilla* had longer lateral branches with longer internodes than plants of 'Sunparaoros'.
2. Plants of the new *Mandevilla* had larger leaves than plants of 'Sunparaoros'.

3. Plants of the new *Mandevilla* had larger flowers than plants of 'Sunparaoros'.
4. Plants of the new *Mandevilla* and 'Sunparaoros' differed in flower color as plants of 'Sunparaoros' had bright red-colored flowers.
5. Plants of the new *Mandevilla* had shorter peduncles than plants of 'Sunparaoros'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparajapi' grown in a container.

The photograph at the bottom of the sheet is a close-up view of a typical flower and flower buds of 'Sunparajapi'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparajapi'.

Parentage:

*Female, or seed, parent*.—Proprietary selection of *Mandevilla hybrida* identified as code number MH-7, not patented.

*Male, or pollen, parent*.—Proprietary selection of *Mandevilla hybrida* identified as code number MH-31, not patented.

Propagation:

*Type*.—By vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; light brown in color.

*Rooting habit*.—Freely branching; medium density.

Plant description:

*Plant and growth habit*.—Vining plant habit; vigorous growth habit; freely branching habit.

*Lateral branch description*.—Length: About 159 cm. Diameter: About 2.9 mm. Internode length: About 3.6 cm. Strength: Strong, flexible. Texture: Smooth, slightly pubescent; with development, woody. Color, developing: Close to 144A. Color, woody: Close to 199A.

Leaf description:

*Arrangement*.—Opposite, simple.

*Length*.—About 11 cm.

*Width*.—About 5 cm.

*Shape*.—Oblong.

*Apex*.—Cuspidate.

*Base*.—Cordate.

*Margin*.—Entire.

*Texture, upper and lower surfaces*.—Smooth, pubescent

*Venation pattern*.—Pinnate, reticulate.

*Color*.—Developing leaves, upper surface: Close to 137B. Developing leaves, lower surface: Close to 137D. Fully expanded leaves, upper surface: Close to 137A; venation, close to 144B. Fully expanded leaves, lower surface: Close to 137D; venation, close to 144D.

*Petiole length*.—About 1.2 cm.

*Petiole diameter*.—About 2.4 mm.

*Petiole texture, upper and lower surfaces*.—Smooth, pubescent.

*Petiole color, upper and lower surfaces*.—Close to 144A.

Flower description:

*Flower type and habit*.—Single salverform flowers arranged in axillary racemes; flowers face mostly outwardly; freely flowering habit with about two flowers per inflorescence and about 17 to 25 inflorescences developing per plant during the flowering season.

*Natural flowering season*.—Plants begin flowering about six weeks after planting; long flowering period, plants flower continuously from summer to late autumn in Japan.

*Flower longevity on the plant*.—About seven to ten days; flowers not persistent.

*Fragrance*.—None detected.

*Inflorescence height*.—About 13 cm.

*Inflorescence diameter*.—About 13 cm.

*Flowers*.—Appearance: Salverform; flared trumpet, corolla fused and five-parted; flowers roughly star-shaped. Diameter: About 9.8 cm. Depth (length): About 8.4 cm. Throat diameter: About 2.1 cm. Tube length: About 5 cm. Tube diameter, mid-section: About 1.1 cm. Tube diameter, base: About 3.8 mm.

*Flower buds*.—Height: About 7.7 cm. Diameter: About 1.6 cm. Shape: Lenticular. Color: Towards the apex, close to 65D; towards the base, close to 65A.

*Corolla*.—Quantity and arrangement: Five petals arranged in a single whorl and fused towards the base into an elongated tube. Petal lobe length: About 4 cm. Petal lobe width: About 4.3 cm. Petal lobe shape: Orbicular. Petal lobe apex: Cuspidate. Petal lobe margin: Entire; undulate. Petal lobe texture, upper and lower surfaces: Smooth, glabrous; satiny. Throat texture: Smooth, glabrous; satiny. Tube texture: Smooth, glabrous; satiny. Color: Petal lobe, when opening, upper surface: Close to 73D; towards the margins, close to 73C. Petal lobe, when opening, lower surface: Close to N66D; towards the margins, close to 73C. Petal lobe, fully opened, upper surface: Close to 73C; towards the margins, close to N66C. Petal lobe, fully opened, lower surface: Close to 67C; towards the margins, close to N66D. Throat: Close to 20A; towards the base, close to 7B with longitudinal lines, close to 8D. Tube: Close to 68C; towards the base, close to 145B.

*Calyx*.—Quantity and arrangement: Five sepals arranged in a single whorl, fused at the base; calyx, star-shaped. Sepal length: About 5.5 mm. Sepal width: About 2.7 mm. Sepal shape: Lanceolate. Sepal apex: Acute. Sepal margin: Entire. Sepal texture, upper and lower surfaces: Smooth, glabrous. Sepal color: When developing, upper and lower surfaces: Close to 145B. Fully opened, upper surface: Close to 145A; towards the apex, tinged with close to 173A. Fully opened, lower surface: Close to 145B.

*Peduncles*.—Length: About 3.7 cm. Diameter: About 2.7 mm. Texture: Smooth, slightly pubescent. Aspect: Mostly outwardly. Color: Close to 138A.

*Pedicels*.—Length: About 1.7 cm. Diameter: About 2 mm. Texture: Smooth, glabrous. Aspect: Mostly outwardly. Color: Close to 63A.

*Reproductive organs*.—Stamens: Quantity and arrangement: Typically five; filaments fused to corolla; anthers, connivent. Anther shape: Ellipsoidal. Anther size: About 1.2 mm by 8.5 mm. Anther color: Close to 3D. Pollen amount: Scarce. Pollen color: Close to 4D. Pistils: Quantity: Typically one. Pistil length: About 2.5 cm. Style color: Close to 145D. Stigma shape: Conical. Stigma color: Close to 145B. Ovary color: Close to 145A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparajapi' as illustrated and described.

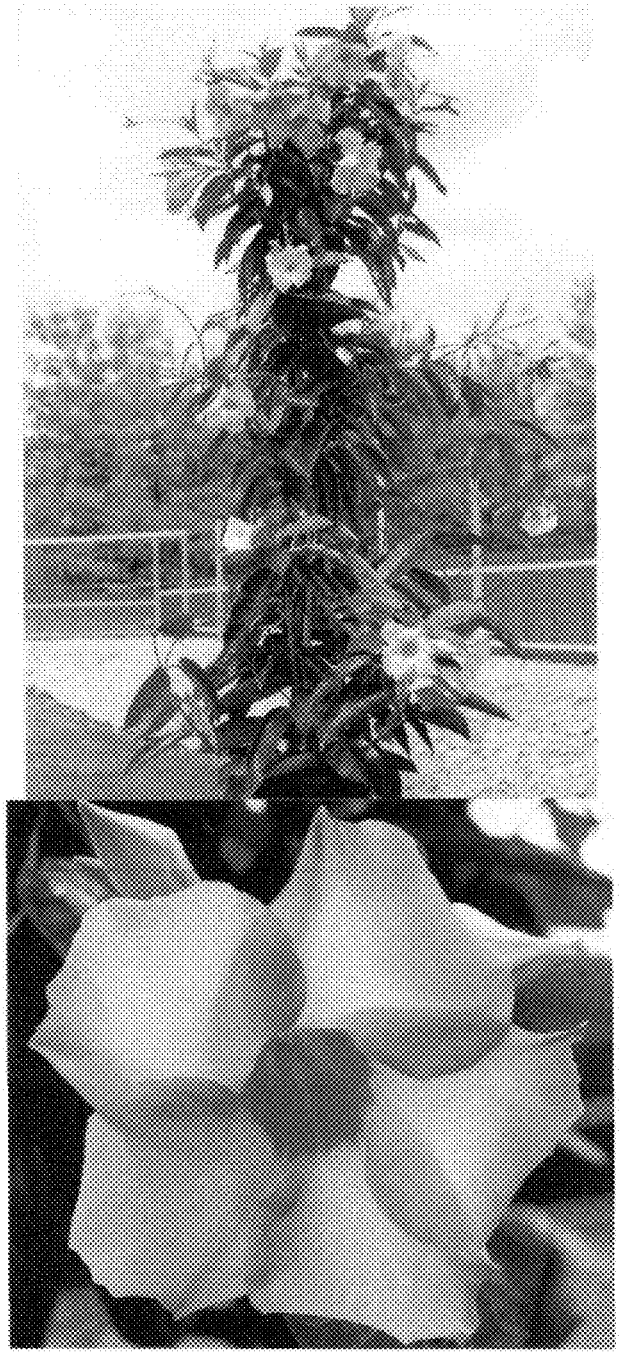

* * * * *